United States Patent

Delonzor et al.

[11] Patent Number: 5,752,914
[45] Date of Patent: May 19, 1998

[54] CONTINUOUS MESH EMI SHIELD FOR PULSE OXIMETRY SENSOR

[75] Inventors: Russell Delonzor, Union City; Al Namy, San Diego, both of Calif.

[73] Assignee: Nellcor Puritan Bennett Incorporated, Pleasanton, Calif.

[21] Appl. No.: 654,449

[22] Filed: May 28, 1996

[51] Int. Cl.⁶ .................................................. A61B 5/00
[52] U.S. Cl. .......................... 600/310; 600/473; 600/476; 442/131
[58] Field of Search ..................... 128/633, 664, 128/665; 428/344, 354; 442/6, 16, 131; 600/310, 322, 323, 344, 473, 476

[56] References Cited

U.S. PATENT DOCUMENTS

| | | | |
|---|---|---|---|
| 4,689,262 | 8/1987 | Bloom | 442/16 |
| 4,988,550 | 1/1991 | Keyser et al. | 428/354 |
| 5,217,013 | 6/1993 | Lewis et al. | 128/633 |
| 5,237,994 | 8/1993 | Goldberger | 128/633 |
| 5,250,342 | 10/1993 | Lang et al. | 428/344 |
| 5,262,229 | 11/1993 | Lampert et al. | 428/344 |

*Primary Examiner*—Jennifer Bahr
*Assistant Examiner*—Eric F. Winaker
*Attorney, Agent, or Firm*—Townsend and Townsend and Crew LLP

[57] ABSTRACT

An improved electromagnetic shield for a photodetector which uses a wire mesh screen laminated to an insulating layer. A portion of the wire mesh screen and laminated layer sandwich can then be cut out to provide an individual electromagnetic shield. The sandwich combination is flexible, and can be easily wrapped around the photodetector. Preferably, an adhesive is on one side of the insulating layer, to allow the wrapped combination to adhere to the photodetector.

21 Claims, 1 Drawing Sheet

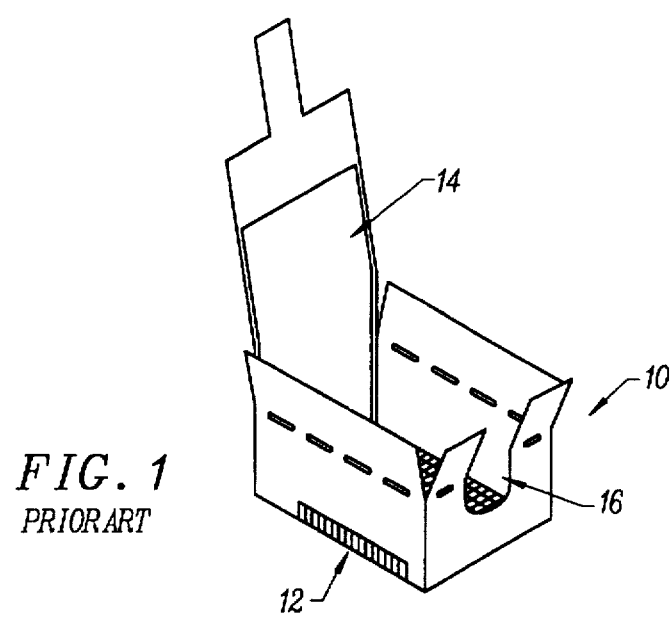
*FIG. 1*
PRIOR ART
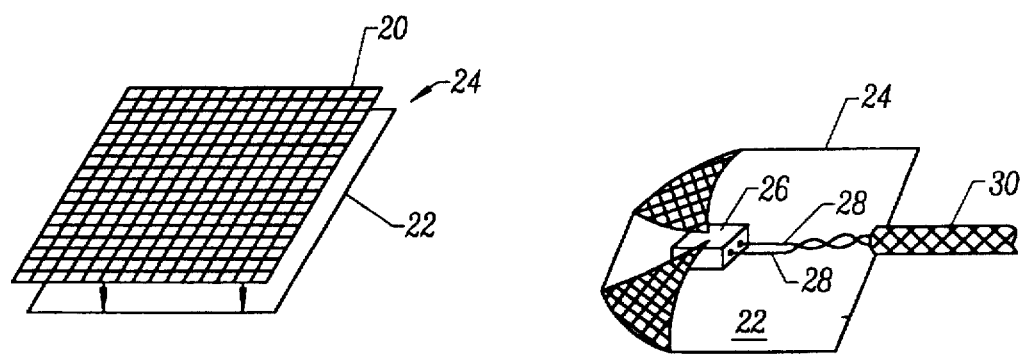
*FIG. 2*
*FIG. 3*
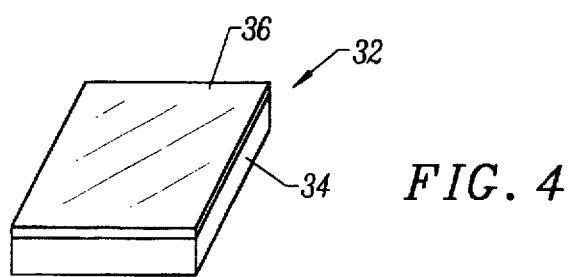
*FIG. 4*

5,752,914

CONTINUOUS MESH EMI SHIELD FOR PULSE OXIMETRY SENSOR

BACKGROUND OF THE INVENTION

The present invention relates to photosensors, and in particular to methods and apparatus for preventing electromagnetic interference with a pulse oximeter photodetector using a Faraday shield.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of blood absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

The detector signal produced by the photodetector can respond not only to light, but can also have current induced by electromagnetic radiation fields. These fields could come from other electrical equipment in the area, for instance. Typically, an electric magnetic shield, or Faraday screen, is placed across the top of the photodetector and grounded to reduce the amount of such electromagnetic coupling into a detector. A trade-off is required, since light must penetrate the screen for the photodetector to operate as desired.

One prior art embodiment is shown in FIG. 1 in which a Faraday cage 10 will enclose a photodetector when the upper portions are folded over the back of the photodetector. A screen 12 will be opposite the face of the photodetector, while the body of the cage is a solid metal, such as copper. An insulating tape 14 is placed on the inside of the metal to avoid shorting to the photodetector. The leads of the photodetector will extend out an opening 16. The manufacturing of such a shield requires that solid metal be etched to produce the screen portion. When placed in a sensor, care must be taken so that the sharp edges of the cage not damage other portions of the sensor.

SUMMARY OF THE INVENTION

The present invention provides an improved electromagnetic shield for a photodetector which uses a wire mesh screen laminated to an insulating layer. A portion of the wire mesh screen and laminated layer sandwich can then be cut out to provide an individual electromagnetic shield. The sandwich combination is flexible, and can be easily wrapped around the photodetector. Preferably, an adhesive is on one side of the insulating layer, to allow the wrapped combination to adhere to the photodetector.

The inventors have determined that such a shield with a wire mesh around all sides of the photodetector is sufficient to reduce the electromagnetic interference. In a preferred embodiment, the wire mesh is copper which is laminated to a pressure sensitive adhesive.

In an alternate embodiment, a tinted plastic is used. The tinting is made of a conductive material having sufficient conductivity to shield against unwanted electromagnetic radiation, while being sufficiently transparent to allow sufficient light of the appropriate wavelengths to pass through the tinted layer to the photodetector. Preferably, the tinted plastic is flexible so that it can be wrapped around the photodetector, and has an adhesive on one side for adhering to the photodetector.

For a fuller understanding of the nature and advantages of the invention, reference should be made to the ensuing description taken in conjunction with the accompanying drawings.

BRIEF DESCRIPTION OF THE DRAWINGS

FIG. 1 is a diagram of a prior art Faraday cage;

FIG. 2 is a diagram of a wire mesh electromagnetic shield according to one embodiment of the present invention;

FIG. 3 is a diagram illustrating the wrapping of a wire mesh shield according to one embodiment of the present invention around a photodetector; and FIG. 4 is a diagram of a tinted plastic electromagnetic shield according to one embodiment of the present invention.

DETAILED DESCRIPTION OF THE PREFERRED EMBODIMENTS

FIG. 2 is a diagram of one embodiment of an electromagnetic shield using a wire mesh screen according to the present invention. A wire mesh screen 20 is shown above an insulating layer 22. The wire mesh screen is preferably composed of copper wires, with the wires having a diameter of between 0.0020 and 0.0024 inches, preferably 0.0022 inches. In addition, the mesh is interwoven at a density of preferably between 75×75 and 125×125 wires per square inch (psi), more preferably 100 wires by 100 wires psi.

Insulating layer 22 is preferably a double sticky adhesive which may be covered with a release liner on both sides. The release liner is peeled off of one side adjacent the copper mesh, and the copper mesh is then laminated to the adhesive. An electromagnetic shield can then be cut from a large sheet by cutting through the wire mesh and the insulating layer 22, but not cutting through the remaining release liner. Subsequently, upon assembly, a particular electromagnetic screen sandwich of a mesh 20 and insulating layer 22 can be peeled off of the release liner and applied to a photodetector.

In one embodiment, the insulating layer 22 is a polyester which is 0.5 mil thick, and is coated with adhesive to a thickness of 1.5 mil on each side.

It has been determined experimentally that a mesh of the above dimensions is sufficient for electromagnetic shielding, while attenuating the desired wavelengths of light by only approximately 40%.

FIG. 3 illustrates the wrapping of a laminated sandwich 24 around a photodetector 26. The insulating layer 22 is placed adjacent the photodetector, and its adhesive will help it stick to the photodetector. In addition, the photodetector has leads 28 extending between the photodetector and a lead shield 30. These unshielded leads between the shield 30 and the photodetector 26 can also be susceptible to electromagnetic interference. Accordingly, the electromagnetic shield 24 is preferably applied around these leads as well.

In one embodiment, the copper mesh is plated to prevent corrosion. Corrosion of the copper mesh will change its color to green, which could effect the calibration of a pulse oximeter sensor which is calibrated for a particular wavelength of the red and infrared light emitters. In one embodiment a tin-lead plating is used.

An advantage of the embodiment of FIGS. 2 and 3 is that the electromagnetic shield is flexible, and can be bent around the photodetector without providing sharp edges as in the prior art cage of FIG. 1.

FIG. 4 is an alternate embodiment of the present invention in which an electromagnetic shield 32 is constructed using an insulating layer 34 having a conductive layer 36 deposited thereon. The additional layer 36 provides a tinted appearance. The coating 36 is sufficiently conductive to reduce the electromagnetic interference, while being sufficiently transparent to allow sufficient light to pass through. Preferably, less than 50% of the light is attenuated and at least 50% of the electromagnetic interference that would be induced into an unprotected photodetector is removed. In one embodiment, layer 34 can be a plastic film and conductive layer 36 could be indium tin oxide. Alternately, a thin silver or other layer could be used.

One difficulty with such a conductive layer is that of connecting a ground wire to the shield, which also must be done for the embodiment of FIGS. 2 and 3. It is difficult to solder a wire to such a conductive layer. Preferably, an alternate method of bonding a wire, such as low temperature curing conductive epoxy or a conducting adhesive is used. Alternately, Z-axis conductive or anisotropic materials could be used. Other alternatives are gas-tight mechanical crimps, zero insertion forced edge connections, staples or rivets. Once formed, the electromagnetic shield of FIG. 4 can be stamped out of a larger sheet and wrapped around a photodetector as in the embodiment of FIG. 3.

As will be understood by those with skill in the art, the present invention may be embodied in other specific forms without departing from the spirit or essential characteristics thereof. Accordingly, the above description is meant to be illustrative, but not limiting, of the scope of the invention which is set forth in the following claims.

What is claimed is:

1. A method for providing an electromagnetic shield for a photodetector, comprising the steps of:
   providing an insulating layer;
   providing a wire mesh screen;
   laminating said wire mesh screen to said insulating layer to produce a laminated sandwich;
   cutting out individual electromagnetic shields from said laminated sandwich; and
   placing one of said electromagnetic shields adjacent said photodetector, with said insulating layer facing said photodetector.

2. The method of claim 1 further comprising the step of providing an adhesive on a side of said insulating layer opposite said wire mesh screen.

3. The method of claim 1 further comprising the step of wrapping said electromagnetic shield around leads to said photodetector up to a shield around said leads.

4. The method of claim 1 wherein said wire mesh screen is copper.

5. The method of claim 4 wherein said wire mesh screen is comprised of wires having a diameter of 0.0020–0.0024 inches, and having a grid of between 75×75 and 125×125 wires per square inch.

6. A method for providing an electromagnetic shield for a photodetector, comprising:
   providing an insulating layer;
   providing a wire mesh screen;
   laminating said wire mesh screen to said insulating layer to produce a laminated sandwich;
   cutting out individual electromagnetic shields from said laminated sandwich; and
   placing one of said electromagnetic shields adjacent said photodetector, with said insulating layer facing said photodetector;
   wherein said insulating layer is a double sided adhesive layer bonded to a release liner on at least one side, wherein said cutting step cuts through said double sided adhesive layer but not said release liner.

7. A method for providing an electromagnetic shield for a photodetector, comprising the steps of:
   providing an insulating layer as a double sided adhesive layer bonded to a release liner;
   providing a copper wire mesh screen;
   laminating said wire mesh screen to said insulating layer to produce a laminated sandwich;
   cutting out individual electromagnetic shields from said laminated sandwich by cutting through said copper wire mesh screen and said insulating layer, but not through said release liner;
   separating one of said electromagnetic shields from said release liner; and
   at least partially enclosing said photodetector with said one of said electromagnetic shields, with a side of said electromagnetic shield having said insulating layer being adjacent said photodetector, and including, within the area wrapped by said electromagnetic shield, leads connected to said photodetector up to a shield around said leads.

8. A sensor comprising:
   a photodetector mounted in said sensor;
   a wire mesh screen; and
   an insulating layer bonded to said wire mesh screen to form an electromagnetic shield, said electromagnetic shield at least partially enclosing said photodetector.

9. The sensor of claim 8 further comprising an adhesive bonded to said insulating layer for holding said electromagnetic shield in position.

10. The sensor of claim 8 wherein said electromagnetic shield is also at least partially enclosing leads of said photodetector up to a shield for said leads.

11. The sensor of claim 8 wherein said wire mesh screen is copper.

12. The sensor of claim 11 wherein said wire mesh screen is comprised of wires having a diameter of 0.0020 inches to 0.0024 inches, and having a grid of between 75×75 and 125×125 wires per square inch.

13. A pulse oximeter sensor comprising:
    a photoemitter mounted in said sensor;

a photodetector mounted in said sensor;

a copper wire mesh screen;

an insulating layer bonded to said wire mesh screen to form an electromagnetic shield, said electromagnetic shield at least partially enclosing said photodetector;

an adhesive bonded to said insulating layer for holding said electromagnetic shield in a wrapped position; and wherein said electromagnetic shield is also at least partially enclosing leads of said photodetector up to a shield for said leads.

14. A sensor comprising:

a photodetector mounted in said sensor;

an insulating layer; and a conductive layer bonded to said insulating layer to form an electromagnetic shield, said electromagnetic shield at least partially enclosing said photodetector;

said conductive layer being sufficiently transparent to block less than 50% of the light directed at said photodetector, and being sufficiently conductive to reduce electromagnetic interference by at least 50% compared to an unshielded photodetector.

15. The sensor of claim 14 further comprising an adhesive bonded to said insulating layer for holding said electromagnetic shield in a wrapped position.

16. The sensor of claim 14 wherein said electromagnetic shield is also wrapped around leads of said photodetector up to a shield for said leads.

17. The sensor of claim 14 wherein said conductive layer is indium tin oxide.

18. The sensor of claim 14 further comprising a ground lead coupled to said conductive layer.

19. The sensor of claim 18 wherein said ground lead is coupled to said conductive layer by a conductive adhesive.

20. The sensor of claim 18 wherein said ground lead is connected to said conductive layer by a low temperature curing conductive epoxy.

21. The sensor of claim 14 wherein said conductive layer is silver.

* * * * *